(12) United States Patent
Ding et al.

(10) Patent No.: US 11,207,127 B2
(45) Date of Patent: Dec. 28, 2021

(54) SURGICAL INSTRUMENTS FACILITATING REPLACEMENT OF DISPOSABLE COMPONENTS AND/OR STERILIZATION OF REUSABLE COMPONENTS

(71) Applicant: COVIDIEN LP, Mansfield, MA (US)

(72) Inventors: Weijiang Ding, Shanghai (CN); Kai Liu, Shanghai (CN)

(73) Assignee: Covidien LP, Mansfield, MA (US)

( * ) Notice: Subject to any disclaimer, the term of this patent is extended or adjusted under 35 U.S.C. 154(b) by 246 days.

(21) Appl. No.: 15/508,962

(22) PCT Filed: Sep. 25, 2014

(86) PCT No.: PCT/CN2014/087414
§ 371 (c)(1),
(2) Date: Mar. 6, 2017

(87) PCT Pub. No.: WO2016/045041
PCT Pub. Date: Mar. 31, 2016

(65) Prior Publication Data
US 2017/0273734 A1    Sep. 28, 2017

(51) Int. Cl.
*A61B 18/14* (2006.01)
*A61B 34/35* (2016.01)
(Continued)

(52) U.S. Cl.
CPC .......... *A61B 18/1445* (2013.01); *A61B 17/29* (2013.01); *A61B 34/35* (2016.02);
(Continued)

(58) Field of Classification Search
CPC ...... A61B 18/1442–1447; A61B 17/29; A61B 17/295; A61B 2090/0813;
(Continued)

(56) References Cited

U.S. PATENT DOCUMENTS 5,176,699 A   1/1993   Markham
5,499,992 A   3/1996   Meade et al.
(Continued)

FOREIGN PATENT DOCUMENTS

CN   101066217 A   11/2007
CN   101507623 A   8/2009
(Continued)

OTHER PUBLICATIONS

U.S. Appl. No. 08/926,869, filed Sep. 10, 1997, James G. Chandler.
(Continued)

*Primary Examiner* — Eun Hwa Kim
*Assistant Examiner* — Catherine Premraj
(74) *Attorney, Agent, or Firm* — Carter, DeLuca & Farrell LLP

(57) ABSTRACT

A surgical end effector assembly includes a pair of jaw members, a knife defining a longitudinal slot, a pivot pin coupling the jaw members to one another, and a drive member including a drive pin that is engaged to the jaw members. The pivot pin and/or the drive pin extends through the longitudinal slot of the knife to couple the knife to the jaw members and/or the drive member. The end effector assembly is transitionable between a use position, wherein the knife and drive member are generally aligned with one another to facilitate releasable engagement of the end effector assembly with a surgical instrument, and a cleaning position, wherein the jaw members, knife, and drive member are fanned apart from one another to facilitate cleaning of the end effector assembly. Methods of disengaging and sterilizing end effector assemblies for reuse are also provided.

18 Claims, 6 Drawing Sheets

(51) Int. Cl.
*A61B 17/29* (2006.01)
*A61B 90/00* (2016.01)
*A61B 18/00* (2006.01)
*A61B 34/00* (2016.01)

(52) U.S. Cl.
CPC ....... *A61B 34/76* (2016.02); *A61B 2017/2931* (2013.01); *A61B 2018/0097* (2013.01); *A61B 2018/00184* (2013.01); *A61B 2018/00607* (2013.01); *A61B 2018/00791* (2013.01); *A61B 2018/00875* (2013.01); *A61B 2018/1455* (2013.01); *A61B 2018/1495* (2013.01); *A61B 2090/0813* (2016.02)

(58) Field of Classification Search
CPC .... A61B 2017/2931; A61B 2017/2916; A61B 2017/2919; A61B 2017/2927; A61B 2017/2933; A61B 2017/2936; A61B 2017/2939; A61B 2017/2947; A61B 2018/00184; A61B 2018/00202; A61B 2018/0097; A61B 2018/145–1462; A61B 2018/00607; A61B 2018/00791; A61B 2018/00875; A61B 2018/1495; A61B 34/35; A61B 34/76
See application file for complete search history.

(56) References Cited

U.S. PATENT DOCUMENTS

| | | | |
|---|---|---|---|
| 5,582,617 A | 12/1996 | Klieman et al. | |
| H1745 H | 8/1998 | Paraschac | |
| 5,792,165 A | 8/1998 | Klieman et al. | |
| 5,810,865 A | 9/1998 | Koscher et al. | |
| 5,810,876 A * | 9/1998 | Kelleher | A61B 10/06 606/170 |
| 5,893,874 A | 4/1999 | Bourque et al. | |
| 5,947,996 A * | 9/1999 | Logeman | A61B 17/29 606/205 |
| 5,961,531 A * | 10/1999 | Weber | A61B 17/1611 604/22 |
| 6,059,776 A | 5/2000 | Gatto | |
| 6,086,606 A | 7/2000 | Knodel et al. | |
| H1904 H | 10/2000 | Yates et al. | |
| 6,293,954 B1 | 9/2001 | Fogarty et al. | |
| H2037 H | 7/2002 | Yates et al. | |
| 6,673,092 B1 * | 1/2004 | Bacher | A61B 17/2909 606/205 |
| 7,055,413 B1 | 6/2006 | Wang | |
| 7,208,005 B2 | 4/2007 | Frecker et al. | |
| 7,306,597 B2 | 12/2007 | Manzo | |
| 7,435,249 B2 | 10/2008 | Buysse et al. | |
| 8,251,996 B2 | 8/2012 | Hushka et al. | |
| 8,647,362 B2 | 2/2014 | Griego | |
| 8,679,140 B2 | 3/2014 | Butcher | |
| RE44,834 E | 4/2014 | Dumbauld et al. | |
| 8,827,996 B2 | 9/2014 | Scott et al. | |
| 8,858,554 B2 | 10/2014 | Kerr et al. | |
| 8,894,674 B2 | 11/2014 | Balanev et al. | |
| 8,920,461 B2 | 12/2014 | Unger et al. | |
| 8,939,975 B2 | 1/2015 | Twomey et al. | |
| 8,968,298 B2 | 3/2015 | Twomey | |
| 8,968,311 B2 | 3/2015 | Allen, IV et al. | |
| 8,968,313 B2 | 3/2015 | Larson | |
| 9,011,436 B2 | 4/2015 | Garrison | |
| 9,023,039 B2 | 5/2015 | Kerr | |
| 9,034,009 B2 | 5/2015 | Twomey et al. | |
| 9,039,691 B2 | 5/2015 | Moua et al. | |
| 9,072,524 B2 | 7/2015 | Heard et al. | |
| 9,113,901 B2 | 8/2015 | Allen, IV et al. | |
| 9,113,904 B2 | 8/2015 | Kerr et al. | |
| 9,113,905 B2 | 8/2015 | McKenna et al. | |
| 9,113,906 B2 | 8/2015 | Mueller | |
| 9,161,769 B2 | 10/2015 | Stoddard et al. | |
| 9,161,812 B2 | 10/2015 | Kerr | |
| 9,192,421 B2 | 11/2015 | Garrison | |
| 9,192,432 B2 | 11/2015 | Larson et al. | |
| 9,192,433 B2 | 11/2015 | Kerr et al. | |
| 9,265,569 B2 | 2/2016 | Hart et al. | |
| 9,265,573 B2 | 2/2016 | Kerr | |
| 9,301,798 B2 | 4/2016 | Kerr et al. | |
| 9,318,691 B2 | 4/2016 | Horner et al. | |
| 9,364,247 B2 | 6/2016 | Bucciaglia et al. | |
| 9,375,258 B2 | 6/2016 | Kendrick | |
| 9,375,282 B2 | 6/2016 | Nau, Jr. et al. | |
| 9,433,461 B2 | 9/2016 | Arya et al. | |
| 9,492,223 B2 | 11/2016 | Kerr | |
| 9,510,891 B2 | 12/2016 | Allen, IV et al. | |
| 9,636,168 B2 | 5/2017 | Payne et al. | |
| 2002/0188220 A1 | 12/2002 | Krzyzanowski | |
| 2004/0054364 A1 | 3/2004 | Aranyi et al. | |
| 2004/0186513 A1 | 9/2004 | Dworschak et al. | |
| 2006/0161190 A1 | 7/2006 | Gadberry et al. | |
| 2007/0027469 A1 | 2/2007 | Smith et al. | |
| 2007/0073341 A1 | 3/2007 | Smith et al. | |
| 2007/0173814 A1 * | 7/2007 | Hixson | A61B 18/1445 606/51 |
| 2008/0091189 A1 | 4/2008 | Carlton | |
| 2009/0182327 A1 | 7/2009 | Unger | |
| 2010/0057085 A1 | 3/2010 | Holcomb et al. | |
| 2011/0046661 A1 * | 2/2011 | Kuehn | A61B 17/1608 606/206 |
| 2011/0060333 A1 | 3/2011 | Mueller | |
| 2011/0184405 A1 | 7/2011 | Mueller | |
| 2013/0105545 A1 * | 5/2013 | Burbank | A61B 17/07207 227/175.1 |
| 2013/0238016 A1 * | 9/2013 | Garrison | A61B 18/1445 606/205 |
| 2013/0274736 A1 | 10/2013 | Garrison | |
| 2013/0289561 A1 | 10/2013 | Waaler et al. | |
| 2013/0296922 A1 | 11/2013 | Allen, IV et al. | |
| 2013/0304066 A1 | 11/2013 | Kerr et al. | |
| 2013/0338613 A1 | 12/2013 | Haggstrom et al. | |
| 2013/0345153 A1 | 12/2013 | Mueller | |
| 2014/0025052 A1 | 1/2014 | Nau, Jr. et al. | |
| 2014/0025053 A1 | 1/2014 | Nau, Jr. et al. | |
| 2014/0025070 A1 | 1/2014 | Kerr et al. | |
| 2014/0066910 A1 | 3/2014 | Nau, Jr. | |
| 2014/0066911 A1 | 3/2014 | Nau, Jr. | |
| 2014/0100564 A1 | 4/2014 | Garrison | |
| 2014/0100568 A1 | 4/2014 | Garrison | |

FOREIGN PATENT DOCUMENTS

| | | |
|---|---|---|
| CN | 104042284 A | 9/2014 |
| CN | 104042288 A | 9/2014 |
| EP | 2036505 B1 | 11/2010 |
| EP | 2258297 A1 | 12/2010 |
| EP | 2399538 A2 | 12/2011 |
| WO | 2006/078661 A1 | 7/2006 |
| WO | 2013181100 A1 | 12/2013 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/731,674, filed Dec. 31, 2012, Siebrecht.
Notification of the First Office Action issued in corresponding Chinese Patent Application No. 201480082077.6 dated Dec. 27, 2018, with English translation, 14 pages.
Chinese Office Action dated Mar. 5, 2019 issued in corresponding CN Appln. No. 201480082078.0.
Chinese Office Action dated Oct. 25, 2019 issued in corresponding CN Appln. No. 201480082078.0. (Summary only).
Chinese Office Action dated Jul. 29, 2020 issued in corresponding CN Appln. No. 201480082078.0. (Summary Only).

\* cited by examiner

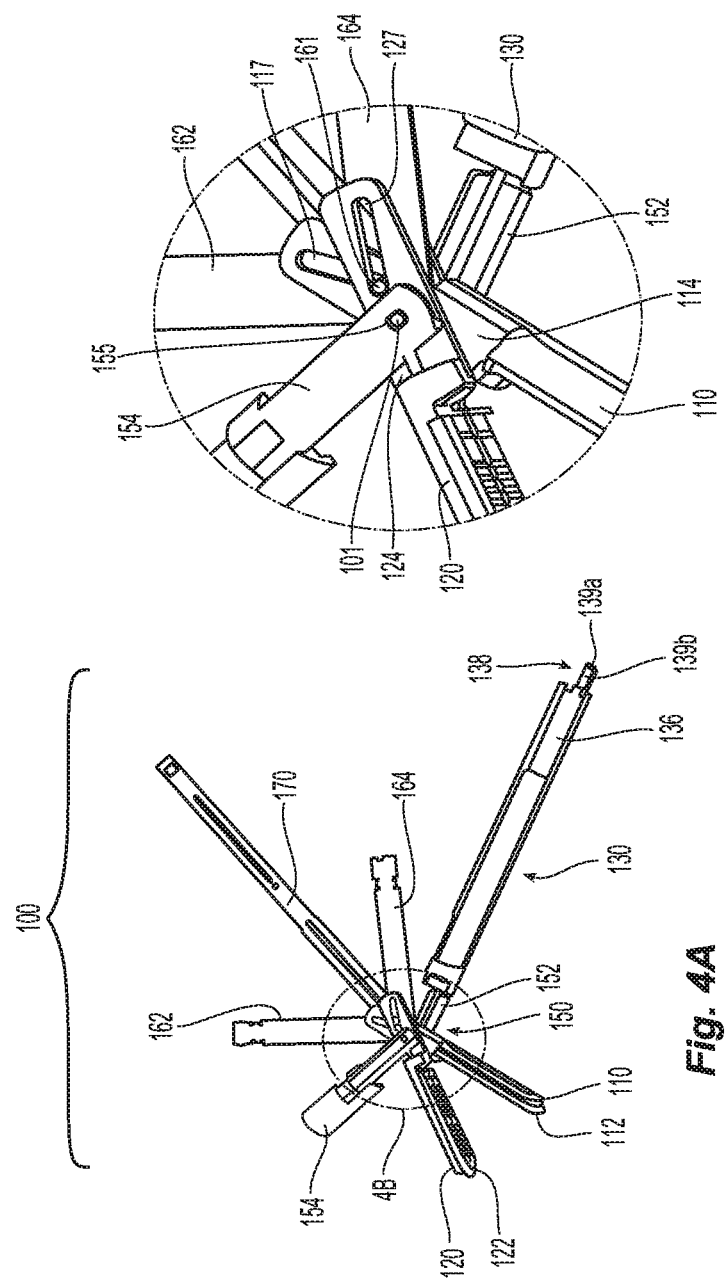

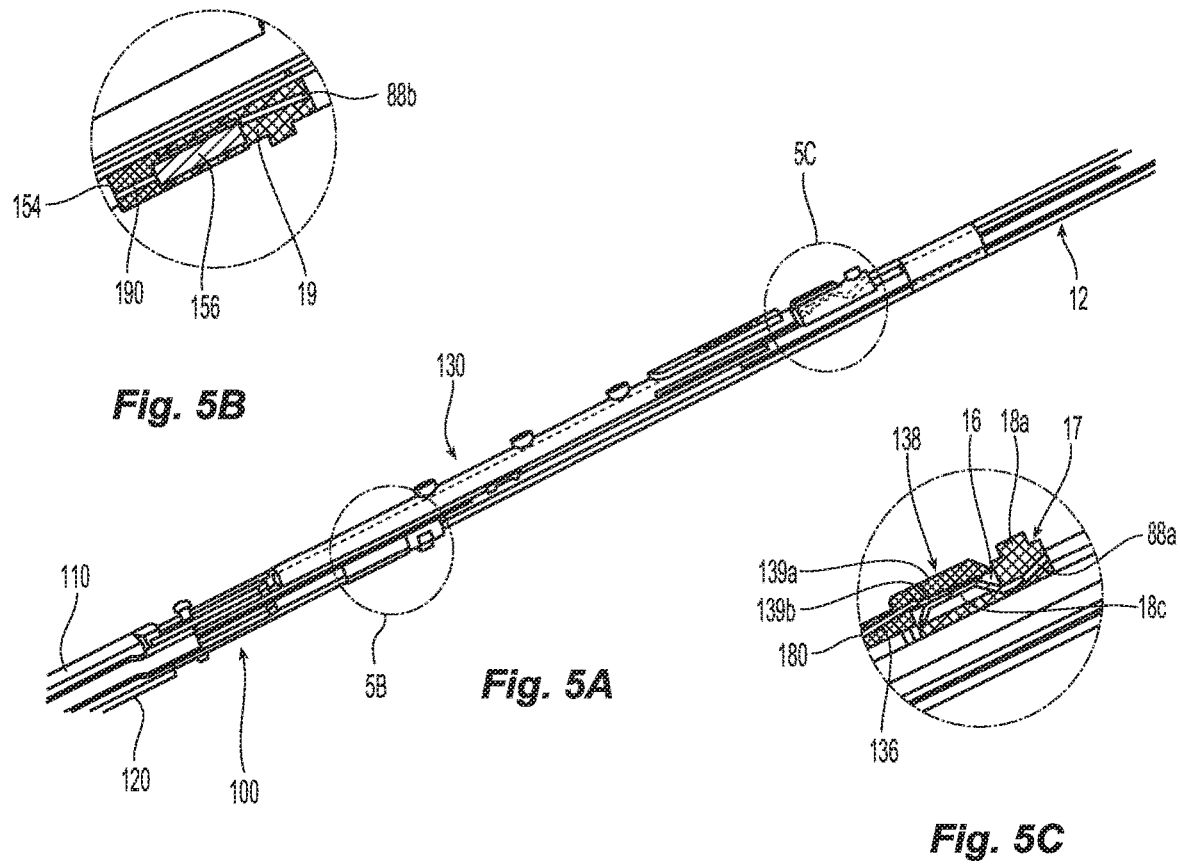
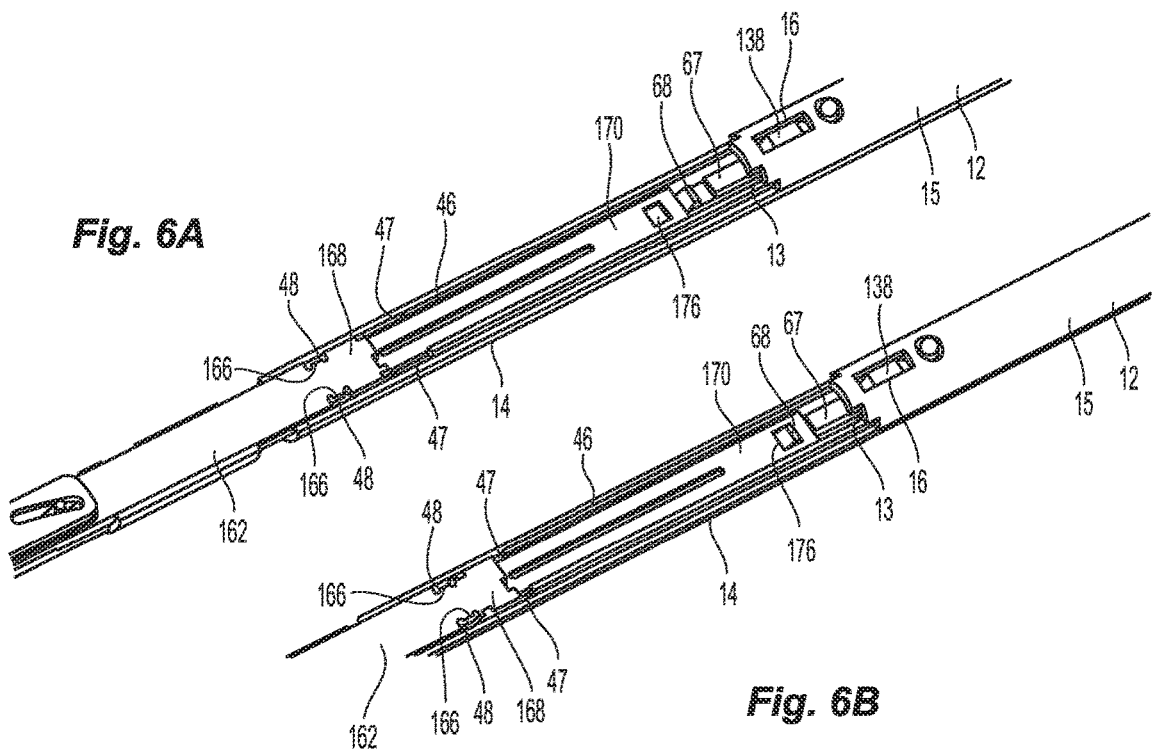

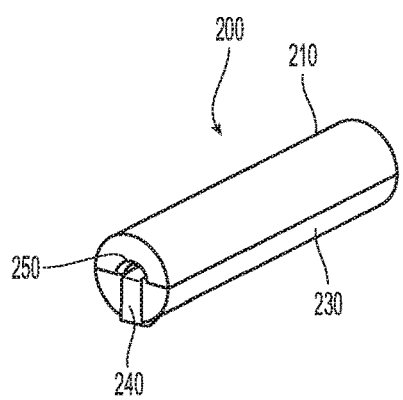
*Fig. 7A*
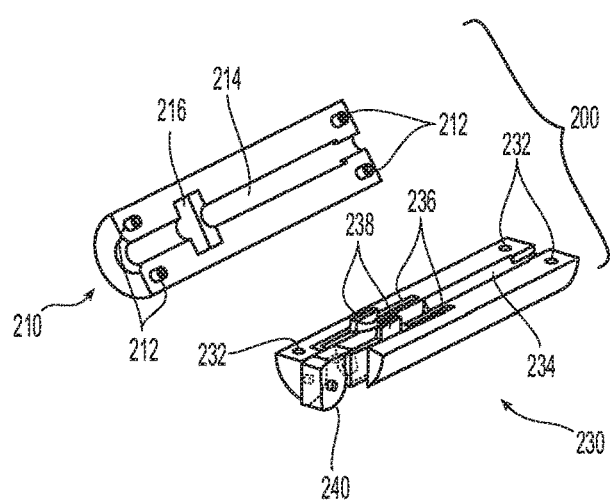
*Fig. 7B*
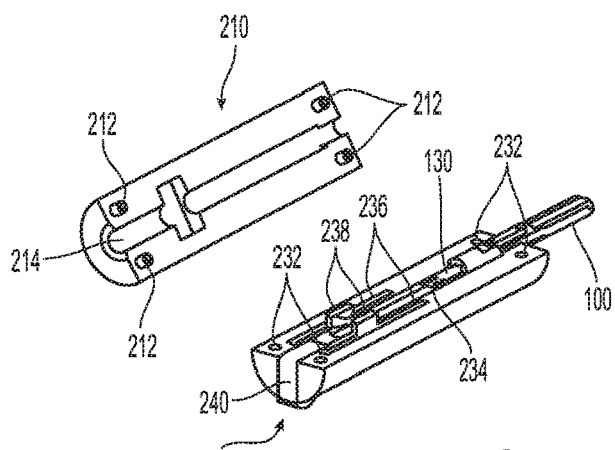
*Fig. 7C*
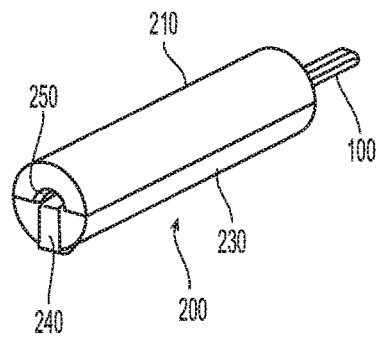
*Fig. 7D*
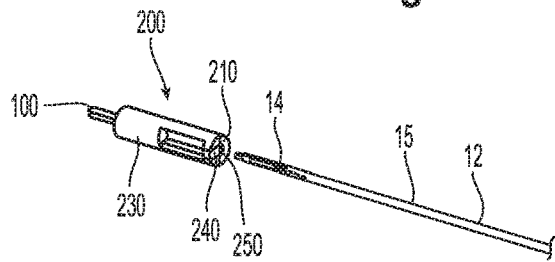
*Fig. 8A*
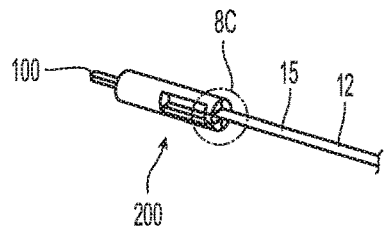
*Fig. 8B*
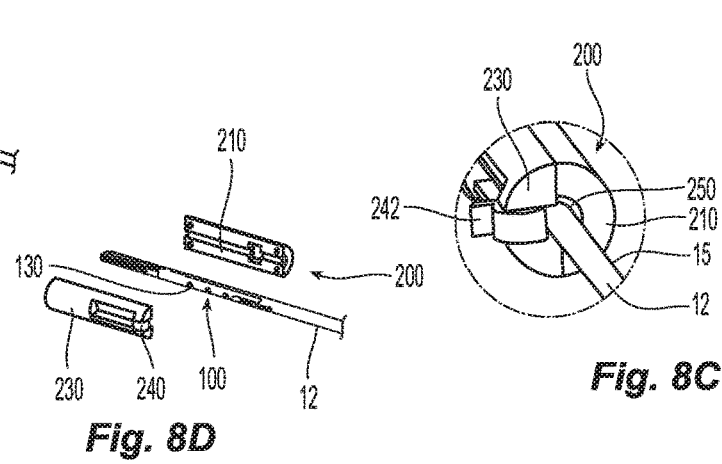
*Fig. 8C*
*Fig. 8D*

SURGICAL INSTRUMENTS FACILITATING REPLACEMENT OF DISPOSABLE COMPONENTS AND/OR STERILIZATION OF REUSABLE COMPONENTS

CROSS REFERENCE TO RELATED APPLICATION

The present application is a U.S. National Stage Application under 35 U.S.C. § 371(a) of PCT/CN2014/087414 filed Sep. 25, 2014. This case is also related to 35 U.S.C. § 371(a) of PCT/CN2014/087418 filed Sep. 25, 2014. The entire contents of which are incorporated by reference herein.

BACKGROUND

Technical Field

The present disclosure relates generally to surgical instruments and, more particularly, to surgical instruments capable of being disassembled to facilitate replacement of any disposable component(s) and/or sterilization of any reusable component(s) of the surgical instrument for reuse.

Background of Related Art

Generally, surgical instruments are classified as disposable, e.g., instruments that are discarded after a single use; partially-reusable or reposable, e.g., instruments including both disposable components that are discarded after a single use and reusable components that are sterilizable for repeated use; or reusable, e.g., instruments that are fully sterilizable for repeated use. As can be appreciated, reusable and partially-reusable surgical instruments help reduce the costs associated with the particular surgical procedures for which they are used. However, although reusable and partially-reusable surgical instruments are cost-effective, the requirements of these reusable and partially-reusable surgical instruments present significant design challenges. More specifically, reusable and partially-reusable surgical instruments must be capable of performing the same functions as their disposable counterparts, resist significant degradation during their useful lives, allow for adequate sterilization of any reusable components, and allow for efficient replacement of any disposable components.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is an end effector assembly for a surgical instrument including first and second jaw members, a knife, a pivot pin, and a drive member. Each of the jaw members defines a jaw body and a jaw flange extending proximally from the jaw body. The knife defines a longitudinal slot. The pivot pin is coupled to the jaw flanges to couple the first and second jaw members to one another. The drive member includes a drive pin coupled to a distal end of the drive member. The drive pin is engaged to the jaw flanges to couple the drive member to the first and second jaw members. The pivot pin and/or the drive pin extends through the longitudinal slot of the knife to couple the knife to the first and second jaw members and/or the drive member, respectively. The end effector assembly is transitionable between a use position, wherein the knife and drive member are generally aligned with one another to facilitate releasable engagement of the end effector assembly with a surgical instrument, and a cleaning position, wherein the first and second jaw members, knife, and drive member are fanned apart from one another about the pivot pin and/or the drive pin to facilitate cleaning of the end effector assembly.

In an aspect of the present disclosure, in the cleaning position, exposed surface areas of the jaw members, knife, and drive member are maximized.

In another aspect of the present disclosure, the end effector assembly further includes one or more jaw supports. The pivot pin is coupled to the jaw support(s). In such aspects, in the use position, the jaw support(s) is generally aligned with the knife and drive member while, in the cleaning position, the jaw support(s), the first and second jaw members, the knife, and the drive member are fanned apart from one another about the pivot pin and/or the drive pin.

In yet another aspect of the present disclosure, the end effector assembly further includes a shaft portion. The pivot pin is coupled to the shaft portion. In such aspects, in the use position, the shaft portion is generally aligned with the knife and the drive member, and wherein, in the cleaning position, the shaft portion, the first and second jaw members, the knife, and the drive member are fanned apart from one another about the pivot pin and/or the drive pin.

In still another aspect of the present disclosure, the shaft portion includes a first engagement feature configured to releasably engage a shaft of a surgical instrument. Additionally or alternatively, the drive member may include a second engagement feature configured to releasably engage a drive bar of a surgical instrument. Further still, the knife may include a third engagement feature configured to releasably engage a knife bar of a surgical instrument.

In still yet another aspect of the present disclosure, the first and second jaw members are configured to pivot relative to one another between a spaced-apart position and an approximated position for grasping tissue therebetween.

In another aspect of the present disclosure, the first jaw member and/or the second jaw member includes an electrically-conductive surface adapted to connect to a source or energy for supplying energy to tissue grasped between the first and second jaw members to treat tissue.

In yet another aspect of the present disclosure, the knife is selectively translatable relative to the first and second jaw members between a retracted position, wherein the knife is disposed proximally of the jaw bodies of the first and second jaw members, and an extended position, wherein the knife extends at least partially between the first and second jaw members to cut tissue grasped therebetween.

A method provided in accordance with aspects of the present disclosure includes disengaging an end effector assembly from a surgical instrument and transitioning the end effector assembly from a use position, wherein components thereof are disposed in general alignment with one another, to a cleaning position, wherein the components are fanned apart from one another.

In an aspect of the present disclosure, the method further includes sterilizing the end effector assembly with the end effector assembly disposed in the cleaning position.

In another aspect of the present disclosure, the components of the end effector assembly include first and second jaw members and a drive member. The first and second jaw members are coupled to one another via a pivot pin, while the drive member is coupled to the first and second jaw members via a drive pin. The method further includes, in such aspects, fanning apart the first and second jaw members and the drive member about the pivot pin and the drive pin to transition the end effector assembly to the cleaning position.

In still another aspect of the present disclosure, the method includes translating a drive bar of the surgical instrument to thereby translate the drive member to pivot the first and second jaw members from a spaced-apart position to an approximated position to grasp tissue therebetween. In such aspects, disengaging the end effector assembly may include disengaging the drive member from the drive bar of the surgical instrument.

In yet another aspect of the present disclosure, the method includes supplying energy, via wires of the surgical instrument and first and second leads of the respective first and second jaw members, to the first and second jaw members to treat tissue grasped therebetween. In such aspects, disengaging the end effector assembly may include decoupling the first and second electrical leads of the first and second jaw members from the wires of the surgical instrument.

In still yet another aspect of the present disclosure, the end effector assembly includes a knife defining a longitudinal slot. The pivot pin and/or the drive pin extend through the longitudinal slot of the knife to couple the knife to the end effector assembly. In such aspects, the method may further include translating a knife bar of the surgical instrument to advance the knife between the first and second jaw members to cut tissue grasped therebetween. Further still, in aspects, disengaging the end effector assembly may include disengaging the knife from the knife bar of the surgical instrument.

BRIEF DESCRIPTION OF THE DRAWINGS

Various aspects and features of the present disclosure are described hereinbelow with reference to the drawings wherein like reference numerals identify similar or identical elements:

FIG. 4A is a perspective view of the end effector assembly of the forceps of FIG. 1A, disposed in a cleaning and/or sterilization configuration;

FIG. 4B is an enlarged, perspective view of the area of detail indicated as "4B" in FIG. 4A;

FIG. 5A is a perspective view of the engagement area of the end effector assembly and shaft of the forceps of FIG. 1A, shown with parts removed to illustrate the electrical connections between the end effector assembly and shaft;

FIG. 5B is an enlarged, perspective view of the area of detail indicated as "5B" in FIG. 5A;

FIG. 5C is an enlarged, perspective view of the area of detail indicated as "5C" in FIG. 5A;

FIGS. 6A and 6B are perspective views of the engagement area of the end effector assembly and shaft of the forceps of FIG. 1A, shown with parts removed to illustrate the mechanical engagement between the end effector assembly and shaft;

FIG. 7A is a perspective view of an assembly tool provided in accordance with the present disclosure and configured to facilitate engagement of the end effector assembly and shaft of the forceps of FIG. 1A;

FIGS. 7B-7D are perspective views of the assembly tool of FIG. 7A illustrating engagement of the end effector assembly of the forceps of FIG. 1A therein;

FIGS. 8A, 8B, and 8D are perspective views illustrating use of the assembly tool of FIG. 7A for engaging the end effector assembly of the forceps of FIG. 1A with the shaft of the forceps of FIG. 1A; and FIG. 8C is an enlarged, perspective view of the area of detail indicated as "8C" in FIG. 8B.

DETAILED DESCRIPTION

Figure 1:
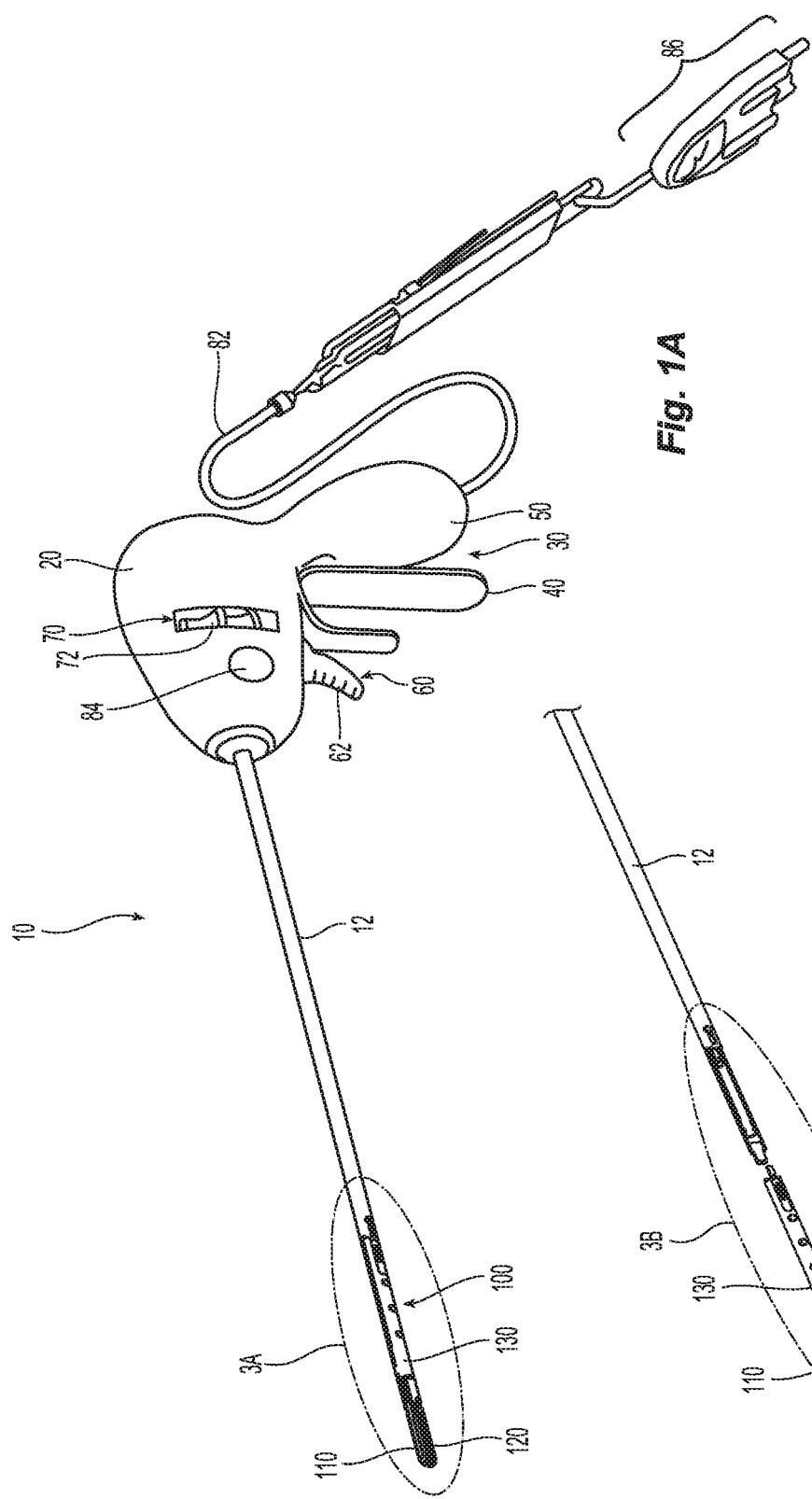
FIG. 1A is a perspective view of an endoscopic surgical forceps provided in accordance with the present disclosure.
FIG. 1B is a perspective view of the distal end of the forceps of FIG. 1A with the end effector assembly disengaged from the shaft.

Turning to FIGS. 1A-8D, an endoscopic surgical forceps provided in accordance with the present disclosure is shown generally identified by reference numeral 10. As described in greater detail below, forceps 10 is configured for selective disassembly to facilitate replacement of any disposable component(s) of forceps 10 and/or sterilization of any reusable component(s) of forceps 10. The selective disassembly of forceps 10 also enables customization in that it allows a user to select a particular component or components for use in accordance with a particular surgical procedure to be performed, a patient's anatomy or condition, a surgeon's preference, and/or other factors. Although detailed herein with respect to forceps 10, the aspects and features of the present disclosure are equally applicable for use with any suitable surgical instrument incorporating disposable, reusable, and/or replaceable components.

Referring to FIGS. 1A-4B, forceps 10 includes a housing 20, a handle assembly 30, a trigger assembly 60, a rotating assembly 70, and an end effector assembly 100. Forceps 10 further includes a shaft 12 having a distal end configured to releasably engage end effector assembly 100 and a proximal end that engages housing 20. More specifically, as will be described in greater detail below, end effector assembly 100 is releasably engagable with shaft 12 to facilitate replacement of end effector assembly 100 with another end effector assembly of similar or different configuration and/or to facilitate cleaning and/or sterilization of end effector assembly 100 for reuse. Housing 20 houses the internal working components of forceps 10.

Handle assembly 30 includes a movable handle 40 and a fixed handle 50. Fixed handle 50 is integrally associated with housing 20 and movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. As described in greater detail below, movable handle 40 is operably coupled to a drive bar 42 that extends through housing 20 and shaft 12 and is ultimately configured to releasably engage drive member 160 of end effector assembly 100, e.g., upon engagement of end effector assembly 100 with shaft 12, such that movable handle 40, drive bar 42, and drive member 160 cooperate to impart movement of jaw members 110, 120 of end effector assembly 100 between a spaced-apart position, corresponding to the initial position of movable handle 40, and an approximated position, corresponding to the compressed position of movable handle 40, to grasp tissue between jaw members 110, 120.

Trigger assembly 60 includes a trigger 62 that extends from housing 20 and is selectively actuatable relative to housing 20 from an un-actuated position to an actuated position. As described in greater detail below, trigger 62 is operably coupled to a knife bar 64 that extends through housing 20 and shaft 12 and is ultimately configured to releasably engage knife 170 of end effector assembly 100, e.g., upon engagement of end effector assembly 100 with shaft 12, such that trigger 62 and knife bar 64 cooperate to impart movement of knife 170 relative to jaw members 110, 120 between a retracted position, wherein knife 170 is positioned proximally of jaw members 110, 120, and an extended position, wherein knife 170 extends at least partially between jaw members 110, 120 to cut tissue grasped therebetween.

Rotating assembly 70 is mounted within housing 20 and operably coupled to shaft 12. Rotating assembly 70 includes a rotation wheel 72 that is rotatable in either direction relative to housing 20 to effect similar rotation of shaft 12 relative to housing 20. With end effector assembly 100 engaged to shaft 12, rotation of rotation wheel 72 likewise effects rotation of end effector assembly 100 relative to housing 20.

Forceps 10 also includes an electrosurgical cable 82 extending from fixed handle 50 and an activation switch 84 operably mounted on housing 20. Cable 82 includes a plug 86 disposed at the free end thereof for connecting forceps 10 to a generator (not shown) or other suitable power source, although forceps 10 may alternatively be configured as a battery powered instrument. Cable 82 includes a plurality of wires (only wires 88a, 88b (FIGS. 5A-5C) are shown), extending therethrough, at least some of which have sufficient length to extend through housing 20 and shaft 12 in order to couple to corresponding electrical leads 180, 190 of jaw members 110, 120 of end effector assembly 100, e.g., upon engagement of end effector assembly 100 with shaft 12, to provide electrical energy to at least one of the respective electrically-conductive surfaces 112, 122 of jaw members 110, 120 of end effector assembly 100. One or more of the wires (not shown) also operably couple activation switch 84 between the generator (not shown) and electrically-conductive surfaces 112, 122 such that activation switch 84 may be selectively activated to initiate the supply of energy to electrically-conductive surfaces 112, 122.

End effector assembly 100 includes a pair of opposing jaw members 110, 120, a shaft portion 130, a jaw support assembly 150, a drive member 160, a knife assembly 170, and a pair of electrical leads 180, 190. Each jaw member 110, 120 includes a jaw body 111, 121 supporting the respective electrically-conductive surface 112, 122, and a respective proximally-extending jaw flange 114, 124. In some embodiments, a longitudinally-extending knife channel 125 may be defined within one or both of electrically-conductive surfaces 112, 122 of jaw members 110, 120, respectively, to permit reciprocation of knife 170 therethrough to cut tissue grasped between jaw members 110, 120.

Flanges 114, 124 of jaw members 110, 120 each define an aperture 116, 126 and an oppositely-angled cam slot 117, 127. Apertures 116, 126 are configured to receive a pivot pin 101 for pivotably coupling jaw members 110, 120 to one another. Cam slots 117, 127 are configured to receive a drive pin 161 that is coupled to drive member 160 such that translation of drive member 160 relative to jaw members 110, 120 urges drive pin 161 through cam slots 117, 127 to pivot jaw members 110, 120 relative to one another between the spaced-apart position and the approximated position for grasping tissue between surfaces 112, 122 of jaw members 110, 120.

Electrical leads 180, 190 are coupled to respective electrically-conductive surfaces 112, 122 at one end thereof and are configured to ultimately couple with corresponding wires 88a, 88b (FIGS. 5A-5C) upon engagement of end effector assembly 100 with shaft 12 such that energy may be supplied from the generator (not shown) to electrically-conductive surfaces 112, 122 for conducting energy through tissue grasped therebetween to treat, e.g., seal, tissue. In some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. As mentioned above, with end effector assembly 100 engaged with shaft 12, activation switch 84 is operably coupled between the source of energy (not shown) and surfaces 112, 122, thus allowing the user to selectively apply energy to surfaces 112, 122 of jaw members 110, 120, respectively, of end effector assembly 100.

Shaft portion 130 of end effector assembly 100 includes inner and outer semi-tubular members 132, 142. Inner semi-tubular member 132 includes a plurality of protrusions 134 extending outwardly therefrom, while outer semi-tubular member 142 defines a plurality of apertures 144 configured to receive protrusions 134 in snap-fit engagement to secure inner and outer semi-tubular members 132, 142 to one another, although other suitable engagements are also contemplated. Inner semi-tubular member 132 further includes a release button 136 extending proximally therefrom. Release button 136 is integrally formed with or otherwise engaged to inner semi-tubular member 132 in a cantilevered arrangement and is at least partially flexible so as to allow the free end of release button 136 to move relative to inner semi-tubular member 132, e.g., upon depression of release button 136. An engagement tab 138 extends from the free end of release button 136. Engagement tab 138 includes a body portion 139a configured to facilitate mechanical engagement of end effector assembly 100 with shaft 12, and an electrically-conductive contact 139b disposed on an underside of body portion 139a. Electrical lead 180 is coupled to electrically-conductive contact 139b to facilitate electrical coupling of electrically-conductive plate 112 of jaw member 110 with the corresponding wire 88a of forceps 10, as detailed below. Outer semi-tubular member 142 defines a window 146 towards the proximal end thereof within which body portion 139a of engagement tab 138 is at least partially received. Window 146 provides access to release button 136 to permit manual depression of release button 136, as detailed below.

Jaw support assembly 150 includes first and second jaw supports 152, 154 disposed on either side of proximal flanges 114, 124 of jaw members 110, 120, respectively. More specifically, jaw support 152 is positioned adjacent proximal flange 114 of jaw member 110, while jaw support 154 is positioned adjacent proximal flange 124 of jaw member 120. Each jaw support 152, 154 defines an aperture 153, 155 therethrough. Apertures 153, 155 are configured to receive the ends of pivot pin 101, which extends between jaw supports 152, 154 and through apertures 116, 126 of jaw members 110, 120. Jaw support 152 is integrally formed with or otherwise engaged with outer semi-tubular member 142 and extends distally therefrom. Jaw support 154 includes an electrically-conductive male connector 156 retained therein. Electrical lead 190 is coupled to electrically-conductive male connector 156 to facilitate electrical coupling of electrically-conductive plate 122 of jaw member 120 with the corresponding wire 88*b* (FIGS. 5A-5C) of forceps 10, as detailed below.

End effector assembly 100 is designed as a bilateral assembly, i.e., where both jaw member 110 and jaw member 120 are movable relative to one another and to jaw support assembly 150. However, end effector assembly 100 may alternatively be configured as a unilateral assembly, i.e., wherein one of the jaw members 110, 120 is fixed with respect to jaw supports 152, 154, and wherein the other jaw member 110, 120 is movable relative to jaw supports 152, 154 and the fixed jaw 110, 120.

Drive member 160 of end effector assembly 100 includes first and second drive plate segments 162, 164 disposed on either side of knife 170. Drive pin 161 extends through respective apertures 163, 165 defined within drive plate segments 162, 164 of drive member 160 and through a longitudinal slot 172 defined within knife 170 to secure drive plate segments 162, 164 to one another on either side of knife 170. Knife 170 and drive member 160 are slidable relative to one another via translation of drive pin 161 through longitudinal slot 172 of knife 170. As noted above, the ends of drive pin 161 are received within cam slots 117, 127 of jaw members 110, 120 such that translation of drive member 160 relative to jaw members 110, 120 urges drive pin 161 through cam slots 117, 127 to pivot jaw members 110, 120 relative to one another between the spaced-apart position and the approximated position for grasping tissue between surfaces 112, 122. Drive plate segments 162, 164 each further include a neck 166, 168 extending from a proximal end thereof to a respective head 167, 169. Necks 166, 168 define reduced diameters as compared to respective heads 167, 169, the importance of which is detailed below.

Knife 170 defines a distal cutting edge 174, a proximal aperture 176 to enable releasable engagement of knife 170 with knife bar 64, and, as mentioned above, defines a longitudinal slot 172 configured to receive pivot pin 101 and drive pin 161 therethrough. In use, as detailed below, knife 170 is selectively translatable between and relative to jaw members 110, 120 to cut tissue grasped therebetween.

Figure 2:
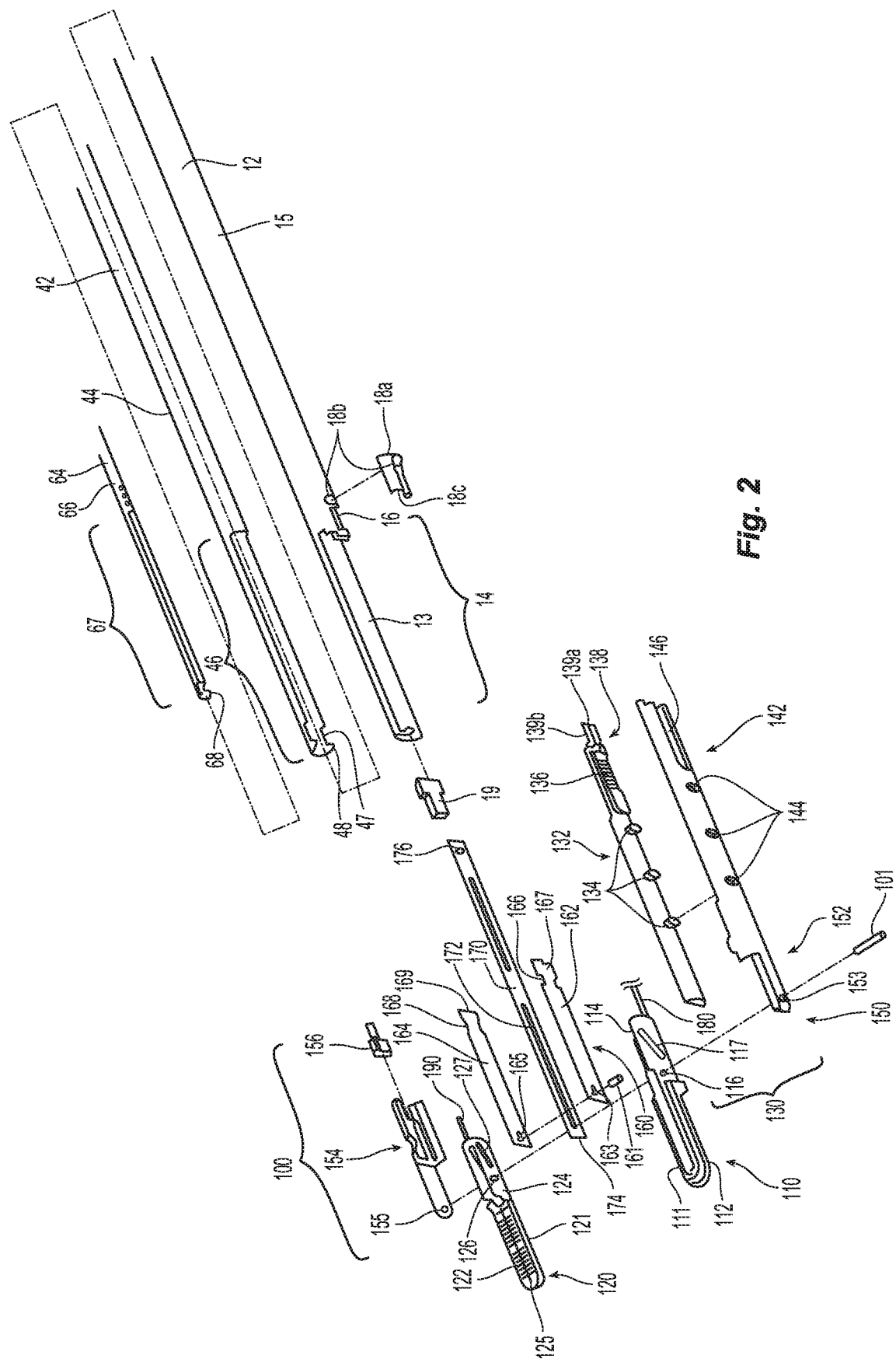
FIG. 2 is an exploded, perspective view of the distal end of the forceps of FIG. 1A.
Figure 3A:
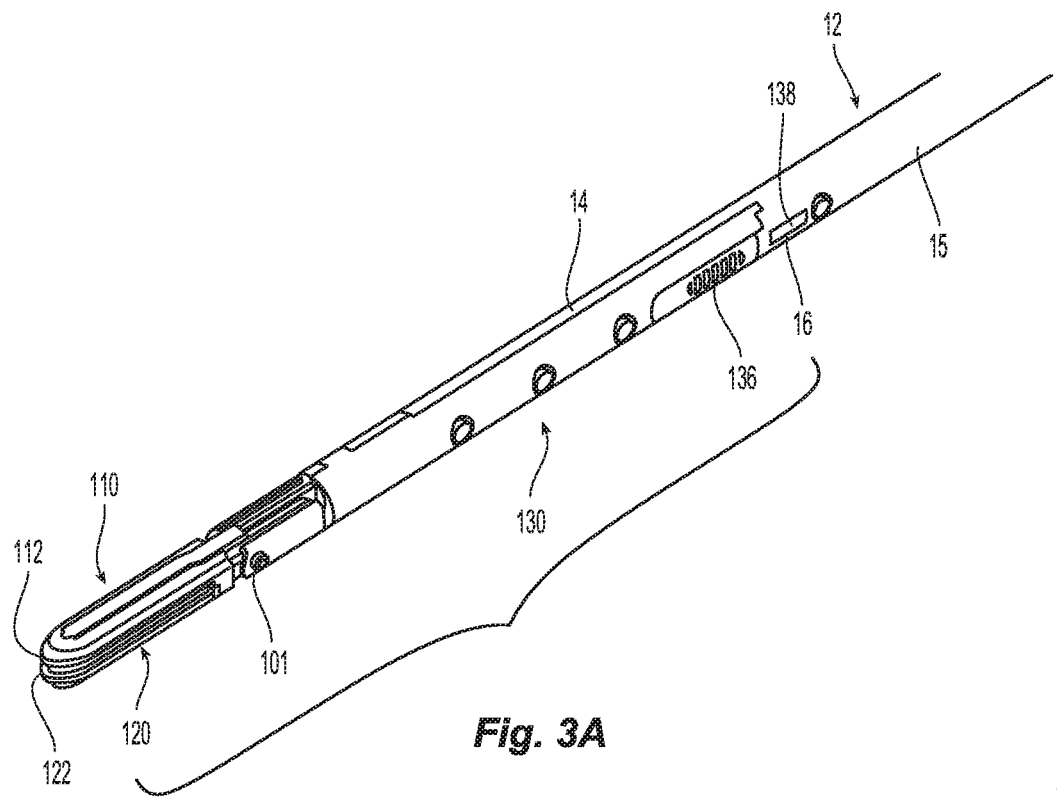
FIG. 3A is an enlarged, perspective view of the area of detail indicated as "3A" in FIG. 1A.
Figure 3B:
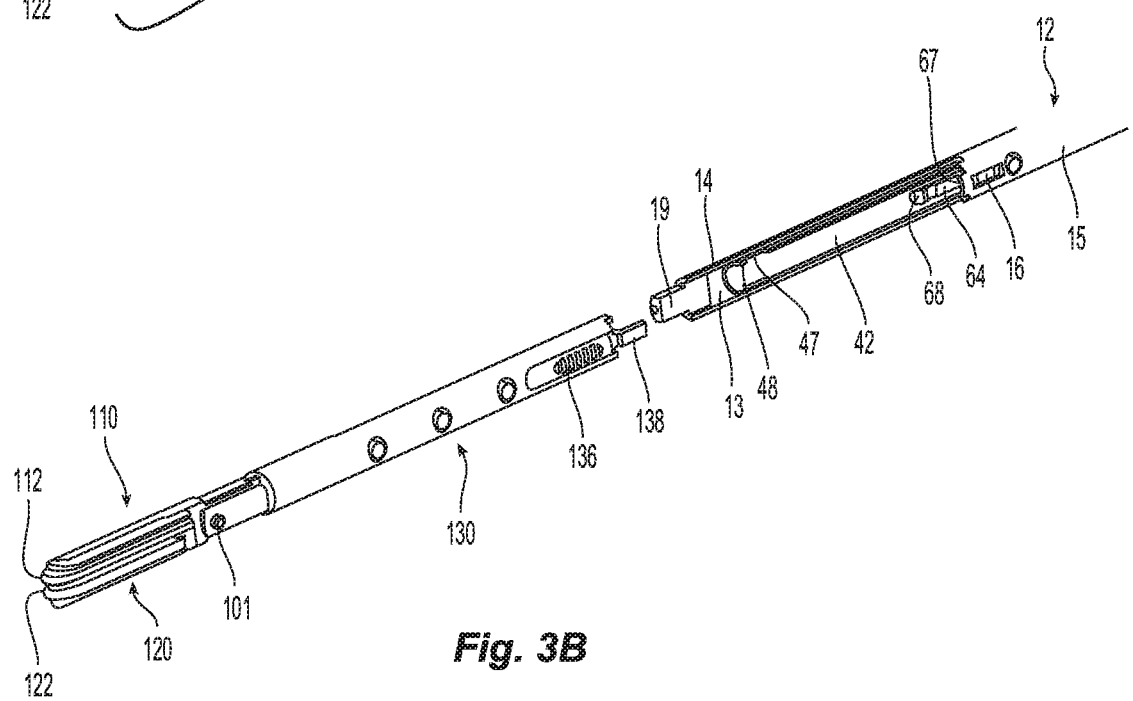
FIG. 3B is an enlarged, perspective view of the area of detail indicated as "3B" in FIG. 1B.

Referring to FIGS. 2, 4A, and 4B, pivot pin 101 extends through respective apertures 116, 126, 153, 155 and through longitudinal slot 172 to pivotably couple jaw member 110, jaw member 120, jaw support 152, jaw support 154, and knife 170 to one another via pivot pin 101. Shaft portion 130 of end effector assembly 100, which is engaged with jaw support 152, is thus also pivotably coupled to jaw member 110, jaw member 120, and jaw support 154 via pivot pin 101. Further, drive pin 161 extends through respective apertures 163, 165 of drive plate segments 162, 164 of drive member 160, longitudinal slot 172 of knife 170, and cam slots 117, 127 of jaw members 110, 120 to couple jaw member 110, jaw member 120, drive plate segment 162, drive plate segment 164, and knife 170 to one another via drive pin 161. As a result of this configuration, when end effector assembly 100 is disengaged from shaft 12, the various components thereof, e.g., jaw member 110, jaw member 120, jaw support 152 and shaft portion 130, jaw support 154, drive plate segment 162, drive plate segment 164, and knife 170, may be fanned apart about pivot pin 101 and/or drive pin 161 to expose the maximum amount of surface area of each of these components. End effector assembly 100 may be autoclaved or otherwise sterilized or cleaned in this fanned-apart position, wherein the maximum surface-area exposure of the various components facilitates cleaning and/or sterilization without the need to disassemble end effector assembly 100. In some embodiments, the various components of end effector assembly 100 may be manipulated to define other fanned-apart configurations during the cleaning and/or sterilization processes or between steps thereof to further facilitate cleaning and/or sterilization.

With reference to FIGS. 1A-6B, as noted above, end effector assembly 100 is configured to releasably engage with forceps 10 at the distal end of shaft 12. More specifically, and as detailed below, shaft 12, drive bar 42, and knife bar 64 are configured to releasably engage engagement tab 138 of release button 136, drive plate segments 162, 164 of drive member 160, and knife 170, respectively, of end effector assembly 100 such that, upon engagement, shaft portion 130 is secured in position via shaft 12, movable handle 40 is operable to pivot jaw members 110, 120 relative to one another, and trigger 62 is operable to advance and retract knife 170. Further, as also detailed below, wires 88*a*, 88*b* (FIGS. 5A-5C) corresponding to electrically-conductive surfaces 112, 122 terminate in a contact 18*c* and female connector 19, respectively, such that, upon engagement of end effector assembly 100 with shaft 12, contact 18*c* and female connector 19 are electrically coupled with respective contact 139*b* and male connector 156 to electrically couple wires 88*a*, 88*b* (FIGS. 5A-5C) with the corresponding electrically-conductive surfaces 112, 122 of jaw members 110, 120.

Shaft 12 of forceps 10 defines a cut-out 13 such that a distal portion 14 of shaft 12 defines a semi-tubular configuration. The semi-tubular configuration of distal portion 14 of shaft 12 cooperates with shaft portion 130 of end effector assembly 100, when end effector assembly 100 is engaged to shaft 12, such that body portion 15 of shaft 12 and the cooperating distal portion 14 of shaft 12 and shaft portion 130 of end effector assembly 100 fully form a tubular shaft member extending between housing 20 and jaw members 110, 120.

Body portion 15 of shaft 12 defines a window 16 adjacent distal portion 14 of shaft 12. A cap 17 defining a body 18*a* is configured to engage body portion 15 of shaft 12 via a pin-aperture engagement 18*b*. Cap 17 includes an electrically-conductive spring contact 18*c* (FIG. 5C) extending from an underside of body 18*a* and positioned such that, when cap 17 is engaged to body portion 15 of shaft 12, spring contact 18*c* extends at least partially into window 16 (see FIG. 5C). As detailed below, upon engagement of end effector assembly 100 with shaft 12, spring contact 18*c* is biased into mating electrical communication with contact 139*b* of engagement tab 138 (FIG. 5C). A female connector 19 is secured at the distal end of distal portion 14 of shaft 12. As also detailed below, upon engagement of end effector assembly 100 with shaft 12, female connector 19 is configured to at least partially receive male connector 156 of jaw support 154 in electrical communication therewith (see FIG. 5B).

Drive bar 42 defines a generally tubular body portion 44 and a semi-tubular distal portion 46 that extends distally from body portion 44. A neck 47 extends from a distal end of distal portion 46 of drive bar 42 to a head 48. Neck 47 defines reduced diameter as compared to head 48 such that, as detailed below, upon engagement of end effector assembly 100 with shaft 12, neck 47 is configured to receive heads 167, 169 of drive plate segments 162, 164 of drive member 160 and necks 166, 168 of drive plate segments 162, 164 of drive member 160 are configured to receive head 48 of drive bar 42 to operably engage drive bar 42 and drive member 160 with one another.

Knife bar 64 defines a generally tubular body portion 66 and a semi-tubular distal portion 67 that extends distally from body portion 66. An engagement finger 68 extends distally from semi-tubular distal portion 67 of knife bar 64. As detailed below, upon engagement of end effector assembly 100 with shaft 12, engagement finger 68 is received within aperture 176 of knife 170 to operably engage knife bar 64 and knife 170 with one another.

Referring again to FIGS. 1A-6B, the engagement of end effector assembly 100 with shaft 12 in preparation for use of forceps 10 is described. Initially, shaft portion 130 of end effector assembly 100 is oriented relative to shaft 12 such that the generally planar surfaces of semi-tubular distal portion 14 of shaft 12 and semi-tubular shaft portion 130 of end effector assembly 100 oppose one another.

Thereafter, end effector assembly 100 is slid proximally relative to shaft 12 sufficiently such that engagement tab 138 of end effector assembly 100 is at least partially received, e.g., in snap-fit engagement, within window 16 of shaft 12 between spring contact 18c and body 18a of cap 17, such that engagement finger 68 of knife bar 64 is received within aperture 176 of knife 170, such that neck 47 of drive bar 42 receives heads 167, 169 of drive plate segments 162, 164 and necks 166, 168 of drive plate segments 162, 164 receive head 48 of drive bar 42, and such that female connector 19 at least partially receives male connector 156 of jaw support 154. Upon receipt of engagement tab 138 within window 16 between spring contact 18c and body 18a of cap 17, spring contact 18c is biased into mating engagement with contact 139b of engagement tab 138. Thus, sufficient proximal sliding of end effector assembly 100 relative to shaft 12 mechanically engages shaft portion 130 with shaft 12, mechanically engages drive bar 42 with drive plate segments 162, 164, mechanically engages knife bar 64 with knife 170, electrically couples electrical leads 180, 190 with corresponding wires 88a, 88b.

Once end effector assembly 100 is engaged with shaft 12 as detailed above, forceps 10 is ready for use. With respect to the use of forceps 10, e.g., for grasping, treating, and/or cutting tissue, with jaw members 110, 120 disposed in the spaced-apart position, end effector assembly 100 may be maneuvered into position, e.g., via manipulating housing 20 and/or rotation wheel 72 of rotation assembly 70, such that tissue to be grasped, treated, and/or cut, is disposed between jaw members 110, 120. Next, movable handle 40 is compressed relative to fixed handle 50 to translate drive bar 42 and, thus, drive plate segments 162, 164 relative to jaw members 110, 120 to pivot jaw members 110, 120 relative to one another from the spaced-apart position to the approximated position to grasp tissue therebetween. Thereafter, activation switch 84 may be activated to initiate the supply of energy from the generator (not shown) to electrically-conductive surfaces 112, 122 of jaw members 110, 120, e.g., via wires 88a, 88b, electrical leads 180, 190, and the respective contacts and connectors 18c, 139b and 19, 156 therebetween. More specifically, energy may be supplied to surface 112 of jaw member 110 and/or surface 122 of jaw member 120 and conducted through tissue to treat tissue, e.g., to effect a tissue seal or otherwise treat tissue. Once tissue treatment is complete (or to cut untreated tissue), trigger 62 is actuated to translate knife bar 64 and, thus, knife 170 relative to jaw members 110,120 from the retracted position to the extended position to cut tissue grasped between jaw members 110, 120. When tissue cutting is complete, trigger 62 may be released or returned to return knife 170 to the retracted position. Thereafter, movable handle 40 may be released or returned to return jaw members 110, 120 to the spaced-apart position to release the treated and/or divided tissue. The above may subsequently be repeated in whole or in part, depending upon the particular procedure to be performed.

In order to disengage end effector assembly 100 from shaft 12, e.g., upon completion of the procedure or to engage another (similar or different) end effector assembly with forceps 10, release button 136 is depressed and, while depressing release button 136 (at least initially), end effector assembly 100 is slid distally relative to shaft 12. Depression of release button 136 withdraws engagement tab 138 from window 16 to disengage shaft portion 130 from shaft 12 and, at or near the same time, urges engagement finger 68 from aperture 176 to disengage knife bar 64 from knife 170. Distal sliding of end effector assembly 100 relative to shaft 12 permits decoupling of respective heads 167, 169 and 48 from necks 47 and 166, 168, withdrawal of male connector 156 from female connector 19, and decoupling of contact 139b from contact 18c. As such, by depressing release button 136 and sliding end effector assembly 100 distally relative to shaft 12, end effector assembly 100 may be disengaged from shaft 12.

Once end effector assembly 100 has been fully disengaged from shaft 12, the various components of end effector assembly 100 may pivoted relative to one another to the fanned-apart position (FIGS. 4A and 4B) to facilitate cleaning and/or sterilization of end effector assembly 100. Upon completion of the cleaning and/or sterilization processes, the components of end effector assembly 100 are rotated back into alignment, thus allowing for subsequent engagement of end effector assembly 100 with a sterilized or unused forceps 10.

Turning now to FIGS. 7A-8D, an assembly tool configured to facilitate engagement of end effector assembly 100 with shaft 12 of forceps 10 is shown generally identified by reference numeral 200. Assembly tool 200 is formed from first and second releasably engagable components 210, 230 that cooperate to define a lumen 250 extending longitudinally therethrough. First and second components 210, 230 are releasably engagable with one another via engagement of each of a plurality of protrusions 212 within a respective aperture 232, although other configurations are also contemplated.

Channels 214, 234 defined within first and second components 210, 230 are configured to align with one another to fully form lumen 250 upon engagement of first and second components 210, 230 with one another. One of the channels, e.g., channel 234 of second component 230 is configured to retain semi-tubular shaft portion 130 of end effector assembly 100 therein, while the other channel, e.g., channel 214 of first component 210, is configured to slidably receive semi-tubular distal portion 14 of shaft 12 therein.

Second component 230 further includes a pair of spaced-apart, flexible bands 236 extending along at least a portion of channel 234 on either side thereof. Each band 236 includes a finger 238 extending therefrom in generally perpendicular orientation relative to the respective band 236. Fingers 238 are configured to urge flexible bands 236 apart from one another upon insertion of shaft portion 130 of end effector assembly 100 therebetween. Once shaft portion 130 is seated within channel 234, bands 236 are permitted to return to their initial positions to retain end effector assembly 100 in position within second component 230. First component 210 defines a cavity 216 that opposes fingers 238 and is configured to receive fingers 238 upon engagement of first and second components 210, 230 with one another.

Second component 230 also includes a rotating block 240 pivotably coupled thereto and at least partially disposed within channel 234 thereof. More specifically, rotating block 240 is rotatable between a blocking position (FIG. 7D), wherein rotating block 240 fully occupies channel 234, and an unblocking position (FIG. 8C), wherein rotating block 240 only partially occupies channel 234. Rotating block 240 is initially disposed in the blocking position (FIG. 7D). Further, in the initial, un-flexed positions of bands 236, rotation of rotating block 240 from the blocking position (FIG. 7D) is inhibited. However, upon sufficient insertion of assembly tool 200 about shaft 12, bands 236 are flexed apart from one another to free rotation block 240 such that, upon further insertion of assembly tool 200 about shaft 12, body portion 15 of shaft 12 is permitted to extend into lumen 250 and urge rotation block 240 to rotate to the unblocking position (FIG. 8C). Once the unblocking position (FIG. 8C) has been achieved, assembly tool 200 has been sufficiently inserted about shaft 12 so as to engage end effector assembly 100 with shaft 12. In this unblocking position, tab 242 of rotation block 240 extends from assembly tool 200 to visually indicate to the user that the unblocking position has been achieved and, thus, that end effector assembly 100 is properly engaged with shaft 12.

In use, in order to engage end effector assembly 100 with shaft 12 using assembly tool 200, first and second components 210, 230 are initially disengaged from one another, as shown in FIG. 7B. Thereafter, as shown in FIG. 7C, semi-tubular shaft portion 130 of end effector assembly 100 is urged between fingers 238 and bands 236 of second component 230 and into engagement within channel 234 of second component 230. Once this has been accomplished, first component 210 is then engaged about second component 230, e.g., via engagement of protrusions 212 within apertures 232, as shown in FIG. 7D.

Referring to FIGS. 8A-8C, with end effector assembly 100 engaged within assembly tool 200, assembly tool 200 is advanced proximally over shaft 12 such that semi-tubular distal portion 14 of shaft 12 is inserted into channel 214 of first component 210. Initially, rotation block 240 is disposed in the blocking position (FIG. 8A), thus ensuring that assembly tool 200 and end effector assembly 100 are properly oriented relative to shaft 12 upon insertion of assembly tool 200 about shaft 12. Upon further proximal advancement of assembly tool 200 over shaft 12, the distal end of semi-tubular distal portion 14 of shaft 12 is urged between fingers 238 of second component 230 to flex bands 236 apart from one another (see FIGS. 7B and 7C) and free rotation block 240, thus permitting insertion of body portion 15 of shaft 12 at least partially into lumen 250 of assembly tool 200. As such, body portion 15 of shaft 12 may be inserted into lumen 250 to urge rotation block 240 to rotate to the unblocking position (FIG. 8C). Engagement of end effector assembly 100 with shaft 12 is complete when the unblocking position (FIG. 8C) has been achieved, as evidenced by tab 242 extending from assembly tool 200.

Once end effector assembly 100 has been engaged with shaft 12 as detailed above, first and second components 210, 230 of assembly tool 200 may be disengaged from one another and removed from end effector assembly 100 and shaft 12, as shown in FIG. 8D. In order to disengage end effector assembly 100 from shaft 12 after use, release button 136 (FIGS. 3A and 3B) is utilized, as detailed above.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for a surgical instrument, comprising:

first and second jaw members, each jaw member defining a jaw body and a jaw flange extending proximally from the jaw body;

a knife defining a longitudinal slot;

a pivot pin coupled to the jaw flanges to couple the first and second jaw members to one another; and a drive member including a first drive plate and a second drive plate separate from the first drive plate, the drive member including a drive pin coupled to a distal end of the drive member, the drive pin engaged to the jaw flanges to couple the first drive plate and the second drive plate of the drive member to the first and second jaw members, the pivot pin and the drive pin each extending through the longitudinal slot of the knife to couple the knife to at least one of the first and second jaw members and the first and second drive plates of the drive member, the drive member having a proximal end positioned distal of a proximal end of the knife when the drive member is in use, wherein the end effector assembly is transitionable between a use position, wherein the knife and the drive member are generally aligned with one another to facilitate releasable engagement of the end effector assembly with a surgical instrument, and a cleaning position, wherein each of the first and second jaw members, the knife, and the first and second drive plates of the drive member are radially fanned apart from one another about at least one of the pivot pin or the drive pin to facilitate cleaning of the end effector assembly.

2. The end effector assembly according to claim 1, wherein, in the cleaning position, exposed surface areas of the jaw members, the knife, and the first and second drive plates of the drive member are maximized.

3. The end effector assembly according to claim 1, further including at least one jaw support, the pivot pin coupled to the at least one jaw support, wherein, in the use position, the at least one jaw support is generally aligned with the knife and the first and second drive plates of the drive member, and wherein, in the cleaning position, each of the at least one jaw support, the first and second jaw members, the knife, and the first and second drive plates of the drive member are radially fanned apart from one another about at least one of the pivot pin or the drive pin.

4. The end effector assembly according to claim 1, further including a shaft portion, the pivot pin coupled to the shaft portion, wherein, in the use position, the shaft portion is generally aligned with the knife and the first and second drive plates of the drive member, and wherein, the cleaning position, each of the shaft portion, the first and second jaw members, the knife, and the first and second drive plates of the drive member are radially fanned apart from one another about at least one of the pivot pin or the drive pin.

5. The end effector assembly according to claim 4, wherein the shaft portion includes a first engagement feature configured to releasably engage a shaft of a surgical instrument.

6. The end effector assembly according to claim 5, wherein the drive member includes a second engagement feature configured to releasably engage a drive bar of a surgical instrument.

7. The end effector assembly according to claim 6, wherein the knife includes a third engagement feature configured to releasably engage a knife bar of a surgical instrument.

8. The end effector assembly according to claim 1, wherein the first and second jaw members are configured to pivot relative to one another between a spaced-apart position and an approximated position for grasping tissue therebetween.

9. The end effector assembly according to claim 8, wherein at least one of the first or second jaw members includes an electrically-conductive surface adapted to connect to a source or energy for supplying energy to tissue grasped between the first and second jaw members to treat tissue.

10. The end effector assembly according to claim 8, wherein the knife is selectively translatable relative to the first and second jaw members between a retracted position, wherein the knife is disposed proximally of the jaw bodies of the first and second jaw members, and an extended position, wherein the knife extends at least partially between the first and second jaw members to cut tissue grasped therebetween.

11. A method, comprising:

disengaging an end effector assembly from a surgical instrument;

transitioning the end effector assembly from a use position, wherein components thereof are disposed in general alignment with one another, to a cleaning position, the end effector assembly including:

a knife defining a longitudinal slot, first and second jaw members and a drive member including a first drive plate and a second drive plate separate from the first drive plate, the first and second jaw members coupled to one another via a pivot pin, the first and second drive plates of the drive member coupled to the first and second jaw members via a drive pin, wherein the pivot pin and the drive pin each extend through the longitudinal slot of the knife, the drive member having a proximal end positioned distal of a proximal end of the knife;

fanning each of the first and second jaw members and the first and second drive plates of the drive member radially apart from one another about the pivot pin and or the drive pin to transition the end effector assembly to the cleaning position; and returning the end effector assembly to the use position in which the proximal end of the drive member is positioned distal of the proximal end of the knife.

12. The method according to claim 11, further including sterilizing the end effector assembly with the end effector assembly disposed in the cleaning position.

13. The method according to claim 11, wherein the method includes translating a drive bar of the surgical instrument to thereby translate the first and second drive plates of the drive member to pivot the first and second jaw members from a spaced-apart position to an approximated position to grasp tissue therebetween.

14. The method according to claim 13, wherein the method includes disengaging the end effector assembly by disengaging the drive member from the drive bar of the surgical instrument.

15. The method according to claim 13, wherein the method includes supplying energy, via wires of the surgical instrument and first and second leads of the respective first and second jaw members, to the first and second jaw members to treat tissue grasped therebetween.

16. The method according to claim 15, wherein the method includes disengaging the end effector assembly by decoupling the first and second electrical leads of the first and second jaw members from the wires of the surgical instrument.

17. The method according to claim 11, wherein the method includes translating a knife bar of the surgical instrument to advance the knife between the first and second jaw members to cut tissue grasped therebetween.

18. The method according to claim 17, wherein disengaging the end effector assembly includes disengaging the knife from the knife bar of the surgical instrument.

* * * * *